United States Patent
Kohama et al.

(10) Patent No.: US 10,098,988 B2
(45) Date of Patent: Oct. 16, 2018

(54) MEDICAL DEVICE, AND METHOD FOR PRODUCING MEDICAL DEVICE

(71) Applicant: TERUMO KABUSHIKI KAISHA, Shibuya-ku, Tokyo (JP)

(72) Inventors: Hiromasa Kohama, Hadano (JP); Ayako Tokue, Sendai (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/603,088

(22) Filed: May 23, 2017

(65) Prior Publication Data

US 2017/0258966 A1    Sep. 14, 2017

Related U.S. Application Data

(63) Continuation of application No. PCT/JP2015/082599, filed on Nov. 19, 2015.

(30) Foreign Application Priority Data

Nov. 26, 2014  (JP) ................................. 2014-238975

(51) Int. Cl.
*A61K 9/00* (2006.01)
*A61L 29/08* (2006.01)
(Continued)

(52) U.S. Cl.
CPC ............. *A61L 29/085* (2013.01); *A61L 29/02* (2013.01); *A61L 29/14* (2013.01); *A61L 29/16* (2013.01);
(Continued)

(58) Field of Classification Search
CPC .................................................... A61L 29/085
See application file for complete search history.

(56) References Cited

U.S. PATENT DOCUMENTS 5,670,558 A     9/1997  Onishi et al.
2016/0015869 A1*  1/2016  Omata ................. A61L 29/085
                                                  508/100

FOREIGN PATENT DOCUMENTS

EP     0 693 293 A1    1/1996
JP     6-508645 A      9/1994
(Continued)

OTHER PUBLICATIONS

International Search Report (PCT/ISA/210) dated Jan. 12, 2016, by the Japanese Patent Office as the International Searching Authority for International Application No. PCT/JP2015/082599.
(Continued)

*Primary Examiner* — Paul W Dickinson
(74) *Attorney, Agent, or Firm* — Buchanan Ingersoll & Rooney PC (57) ABSTRACT

A medical device includes a base layer, and a lubrication layer supported on at least a part of the base layer, wherein the lubrication layer contains a block copolymer (A) composed of a first constituting unit derived from a reactive monomer that has an epoxy group and a second constituting unit derived from at least one hydrophilic monomer selected from the group consisting of acrylamide and an acrylamide derivative, and a polymer (B) composed of a constituting unit derived from at least one hydrophilic monomer selected from the group consisting of acrylamide and an acrylamide derivative, wherein the block copolymer (A) is contained in a proportion of 20 to 80% by weight relative to the total weight of the block copolymer (A) and the polymer (B), and wherein the block copolymer (A) is crosslinked or polymerized to form a mesh structure.

20 Claims, 2 Drawing Sheets

(51) Int. Cl.

| | | |
|---|---|---|
| *A61L 29/02* | (2006.01) | |
| *A61L 29/14* | (2006.01) | |
| *A61L 29/16* | (2006.01) | |
| *A61L 31/02* | (2006.01) | |
| *A61L 31/10* | (2006.01) | |
| *A61L 31/14* | (2006.01) | |
| *A61L 31/16* | (2006.01) | |
| *C09D 133/26* | (2006.01) | |
| *C08G 81/02* | (2006.01) | |

(52) U.S. Cl.
CPC ............. *A61L 31/022* (2013.01); *A61L 31/10* (2013.01); *A61L 31/14* (2013.01); *A61L 31/16* (2013.01); *C08G 81/025* (2013.01); *C09D 133/26* (2013.01); *A61L 2400/10* (2013.01)

(56) References Cited

FOREIGN PATENT DOCUMENTS

| JP | 8-24327 A | 1/1996 | |
|---|---|---|---|
| JP | 8-33704 A | 2/1996 | |
| JP | 2000-507997 A | 6/2000 | |
| JP | 2009-525176 A | 10/2014 | |
| JP | WO 2014162872 A1 * | 10/2014 | ........... A61L 29/085 |
| WO | WO 93/00391 A1 | 1/1993 | |
| WO | WO 97/29160 A1 | 8/1997 | |
| WO | 2007/089784 A2 | 8/2007 | |
| WO | 2014/162872 A1 | 10/2014 | |

OTHER PUBLICATIONS

Written Opinion (PCT/ISA/237) dated Jan. 12, 2016, by the Japanese Patent Office as the International Searching Authority for International Application No. PCT/JP2015/082599.

The extended European Search Report dated Jun. 25, 2018, by the European Patent Office in corresponding European Patent Application No. 15864154.8-1109. (6 pages).

* cited by examiner

MEDICAL DEVICE, AND METHOD FOR PRODUCING MEDICAL DEVICE

CROSS-REFERENCES TO RELATED APPLICATIONS

This application is a continuation of International Application No. PCT/JP2015/082599 filed on Nov. 19, 2015, which claims priority to Japanese Patent Application No. 2014-238975, filed on Nov. 26, 2014, the entire contents of which are incorporated herein by reference.

TECHNICAL FIELD

The present invention relates to a medical device and a method for producing the medical device.

BACKGROUND DISCUSSION

Medical devices to be inserted in vivo, such as catheters, guidewires, and indwelling needles, are required to have excellent lubricity in order to reduce tissue damage in blood vessels or the like and also improve the operability for the operator. For this reason, methods for forming a coating of a hydrophilic polymer having lubricity on a surface of a base layer have been developed, and put into practical use. In such a medical device the elution and separation of the hydrophilic polymer from the base layer surface is problematic in terms of maintaining the safety and operability. For this reason, a coating of a hydrophilic polymer is required to have not only excellent lubricity but also durability against loads such as abrasion and scratching.

From such a point of view, Japanese Patent No. JP-A-8-33704 discloses a medical device, which is obtained by dissolving a water-soluble or water-swellable polymer in a solvent that swells a base material of a medical device to produce a polymer solution, immersing a base material of a medical device in the polymer solution to cause swelling, and further crosslinking or polymerizing the polymer on the base material surface, thereby forming a surface lubrication layer on the base material surface.

According to the technique disclosed in Japanese Patent No JP-A-8-33704, a surface lubrication layer having relatively good lubricity can be fixed to a base material.

Japanese Patent No. JP-A-8-33704 discloses that it is preferable to use a block copolymer having a hydrophilic portion that exhibits lubricity and a portion that has an epoxy group for the water-soluble or water-swellable polymer. Further, when such a block copolymer is used, epoxy groups can be crosslinked by a heating operation, whereby a surface lubrication layer that is relatively hard to separate can be formed. However, there is a trade-off relationship between good lubricity and excellent durability, and thus a technique to achieve good lubricity and excellent durability at the same time has been demanded.

In particular, in recent years, medical devices have been made significantly smaller and thinner, and a medical procedure in which a medical device approaches a winding and narrower lesion in vivo has been gaining in popularity. Accordingly, in order to maintain good device operability even in a complicated lesion, there has been a demand for a technique to provide the surface of a device with higher lubricity and durability than before.

Therefore, there has been a demand for a technique to improve both lubricity and durability at the same time so as to support medical procedures that are becoming more complicated and advanced.

SUMMARY

Given the above background, the disclosure herein provides a medical device including a lubrication layer (coating layer) that exerts excellent lubricity and durability, and a method for producing the medical device.

The present inventors have conducted extensive research to address the problems mentioned above. As a result, they found that success can be achieved through a lubrication layer containing a block copolymer of a reactive monomer that has an epoxy group and a hydrophilic monomer and a polymer of a hydrophilic monomer at a specific mixing ratio.

That is, the disclosure herein is directed to a medical device comprising a base layer and a lubrication layer supported on at least a part of the base layer, wherein the lubrication layer contains a block copolymer (A) and a polymer (B), the block copolymer (A) being composed of a first constituting unit derived from a reactive monomer that has an expoxy group and a second constituting unit derived from at least one hydrophilic monomer selected from the group consisting of acrylamide and an acrylamide derivative, and the polymer (B) being composed of a constituting unit derived from at least one hydrophilic monomer selected from the group consisting of acrylamide and an acrylamide derivative, wherein the block copolymer (A) is contained in a proportion of 20 to 80% by weight relative to the total weight of the block copolymer (A) and the polymer (B), and wherein the block copolymer (A) is crosslinked or polymerized to form a mesh structure.

The disclosure is also directed to a method for producing the medical device, comprising dissolving the block copolymer (A) and the polymer (B) in a solvent to prepare a mixture liquid, coating the base layer with the mixture liquid, and then crosslinking or polymerizing the block copolymer (A) in the absence of a catalyst to thereby form the mesh structure on the base layer.

DETAILED DESCRIPTION OF THE EMBODIMENTS

A first exemplary embodiment of the disclosure herein provides a medical device including a base layer and a lubrication layer supported on at least a part of the base layer, wherein: (i) the lubrication layer contains a block copolymer (A) composed of a constituting unit derived from a reactive monomer that has an epoxy group and a constituting unit derived from at least one hydrophilic monomer selected from the group consisting of acrylamide and an acrylamide derivative, and a polymer (B) composed of a constituting unit derived from at least one hydrophilic monomer selected from the group consisting of acrylamide and an acrylamide derivative; (ii) the block copolymer (A) is contained in a proportion of 20 to 80% by weight relative to the total weight of the block copolymer (A) and the polymer (B); and (iii) the block copolymer (A) is crosslinked or polymerized to form a mesh structure.

According to the above configuration, a medical device including a lubrication layer (coating layer) that exhibits excellent lubricity and durability, and a method for producing the medical device are provided. Incidentally, in this description, the constituting unit derived from a reactive monomer that has an epoxy group is also simply referred to as "reactive monomer-derived constituting unit". Similarly, the constituting unit derived from at least one hydrophilic monomer selected from the group consisting of acrylamide and an acrylamide derivative is also simply referred to as "hydrophilic monomer-derived constituting unit". In addition, the block copolymer (A) composed of a reactive monomer-derived constituting unit and a hydrophilic monomer-derived constituting unit is also simply referred to as "block copolymer (A)". Furthermore, the polymer (B) composed of a hydrophilic monomer-derived constituting unit is also simply referred to as "polymer (B)".

With the above configuration, the medical device of the disclosure herein can exhibit excellent surface lubricity and durability (surface lubricity maintaining effect). Lubricity and durability may be obtained by the exemplary embodiments set forth below, but is not limited thereto.

The lubrication layer contains the block copolymer (A) and the polymer (B) [the above clause (i)]. Among them, the block copolymer (A) composing the lubrication layer is composed of a constituting unit derived from a reactive monomer that has an epoxy group and a constituting unit derived from at least one hydrophilic monomer selected from the group consisting of acrylamide and an acrylamide derivative. As used in this description, the constituting unit derived from a reactive monomer that has an epoxy group is also referred to as "constituting unit (A-1)". Similarly, the constituting unit derived from at least one hydrophilic monomer selected from the group consisting of acrylamide and an acrylamide derivative composing the block copolymer (A) is also referred to as "constituting unit (A-2)". Similarly, the constituting unit derived from at least one hydrophilic monomer selected from the group consisting of acrylamide and an acrylamide derivative composing the polymer B) is also referred to as "constituting unit (A-2')". Among them, the constituting unit (A-1) is crosslinked or polymerized with the epoxy group serving as a crosslinking point by a heating (including drying) operation thereby forming a mesh structure (network) [the above clause (iii)]. On the other hand, the other constituting unit (A-2) of the block copolymer (A) and the constituting unit (A-2') of the polymer (B) which compose the lubrication layer exhibit swellability with a solvent, and thus impart lubricity (surface lubricity) under contact with a body fluid or an aqueous solvent. Heretofore, a medical device having a coating layer composed only of the block copolymer (A) as a lubrication layer exhibits high lubricity in an initial stage when a body fluid or an aqueous solvent is brought into contact therewith since the constituting unit (A-2) exists in the mesh of the network formed by the constituting, unit (A-1). However, when the medical device is brought into contact with a lumen wall such as a vascular wall in an operation, the constituting unit (A-2) composing the coating layer is removed from the coating layer due to friction, and the lubricity may be decreased over time. In addition, depending on the composition of the block copolymer (A), a sufficient amount of the constituting unit (A-2) does not enter the mesh of the network formed by the constituting unit (A-1). Thus the constituting unit (A-2) swells little with the body fluid or aqueous solvent in the mesh of the network and swellability is not fully achieved in some cases.

In contrast, according to the disclosure herein, and with respect to lubricity, the block copolymer (A) is contained in a proportion of 20 to 80% by weight relative to the total weight of the block copolymer (A) and the polymer (B) [the above clause (ii)]. With such a specific mixing ratio, in addition to the constituting unit (A-2) derived from the block copolymer (A), a specific amount of the polymer (B) (the constituting unit (A-2)) which is superior to the block copolymer (A) in swellability and lubricity exists inside the mesh of the network formed by the constituting unit (A-1) of the block copolymer (A). For this reason, the lubrication layer (coating layer) according to the present disclosure is superior in lubricity (surface lubricity) and swellability as compared with a coating layer composed only of the block copolymer (A). Even when the medical device is brought in contact with a lumen wall such as a vascular wall in an operation, a sufficient amount of the constituting unit (A-2) or the polymer (B) (the constituting unit (A-2)) exist in the network formed by the constituting unit (A-1), and therefore high lubricity (surface lubricity) can be maintained over a longer period of time (superior in durability). In addition, since the constituting unit (A-2) of the polymer (B) and the constituting units (A-1) and (A-2) of the block copolymer (A) are entangled with each other, strength of the coating layer can be enhanced so that a stronger coating layer can be formed. For this reason, the constituting unit (A-2) derived from the block copolymer (A) and the constituting unit (A-2) derived from the polymer (B) are effectively suppressed or prevented from being removed from the network formed by the constituting unit (A-1) of the block copolymer (A) even when sliding (friction) is applied. Thus, in the medical device according to the exemplary embodiments of the disclosure here, the durability (surface lubricity maintaining effect) can be enhanced.

When a body fluid or an aqueous solvent is brought into contact with the medical device, the constituting unit (A-2) or (A-2') swells in the mesh of the network, and at the same time, the constituting units (A-2) and (A-2') are partially dissolved in the body fluid or aqueous solvent, and there arises a difference in osmotic pressure between the inside and the outside of the mesh (the osmotic pressure inside the mesh becomes higher). Accordingly, a large amount of the body fluid or aqueous solvent penetrates into the mesh. For this reason, in the lubrication layer according to the disclosure, swellability under contact with a body fluid or an aqueous solvent can be significantly enhanced.

In addition, the epoxy groups of the constituting unit (A-1) can be crosslinked or polymerized to form a strong coating layer (lubrication layer). For this reason, the medical device of the disclosure herein has a high strength and can successfully maintain the shape even after sliding. In addition, the epoxy groups of the constituting unit (A-1) can be connected (fixed) to the base layer to suppress or prevent separation from the base layer. For this reason, in the medical device of the disclosure herein, the durability (surface lubricity maintaining effect) can be further enhanced.

Hence, in the medical device according to the disclosure herein, both excellent lubricity (surface lubricity) and excellent durability (surface lubricity maintaining effect) can be achieved.

An exemplary embodiment of the disclosure will be described hereinbelow. Incidentally, the disclosure is not limited only to the following embodiments. The dimensional ratios in the drawings are sometimes magnified for the sake of explanation and may be different from the actual ratios.

In this description, a phrase "X to Y" representing range means "equal to or more than X and equal to or less than Y". Unless otherwise specified, operations and measurements of physical properties and the like are performed under conditions of a room temperature of 20 to 25° C. and a relative humidity of 40 to 50%.

An exemplary embodiment of the medical device according to the disclosure will be described hereinbelow with reference to the appended drawings.

Figure 1:
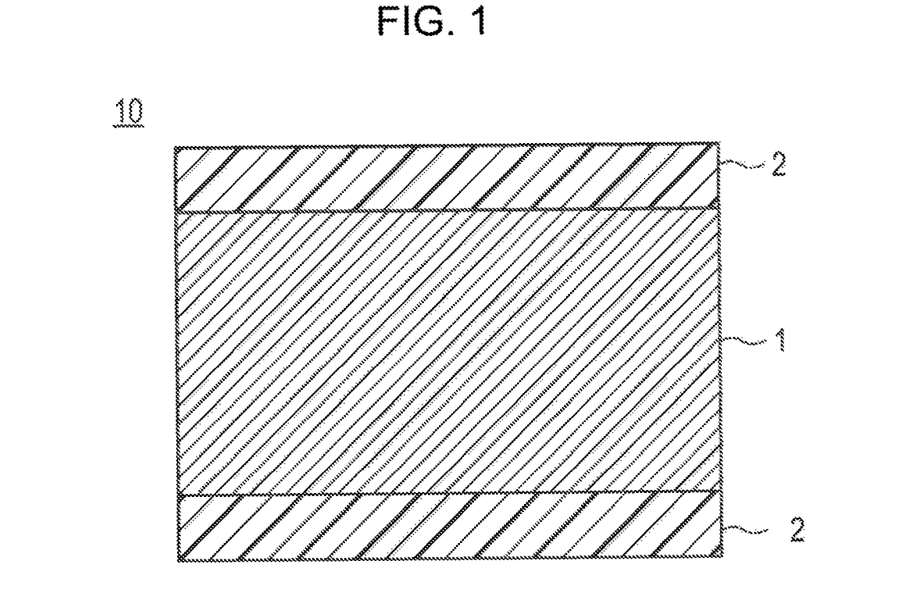
FIG. 1 is a partial sectional view schematically showing a surface laminated structure of an exemplary embodiment of the medical device according to the disclosure.
Figure 2:
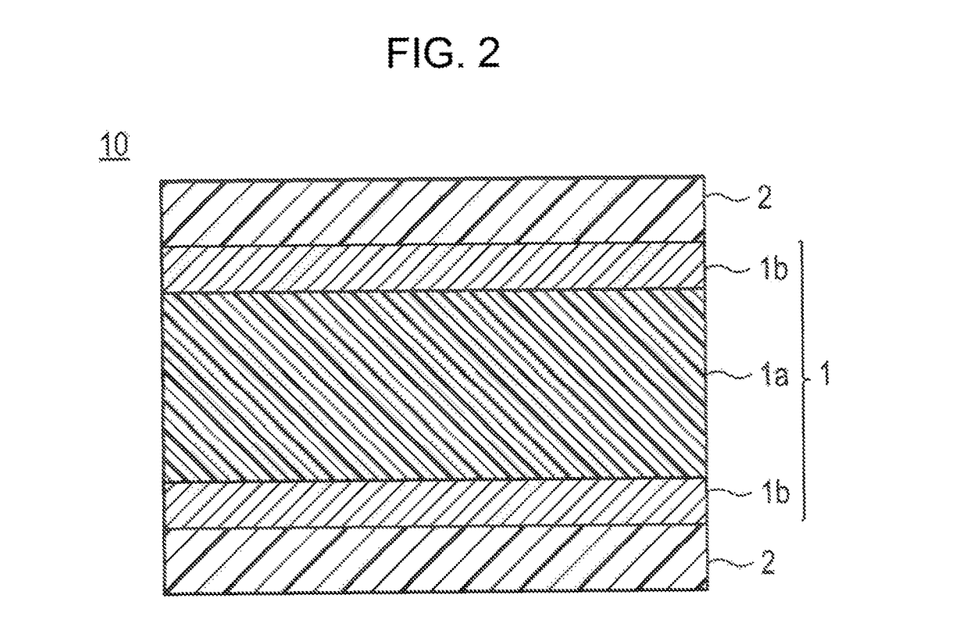
FIG. 2 is a partial sectional view schematically showing a configuration of a surface laminated structure of another exemplary embodiment of the according to the disclosure.

FIG. 1 is a partial sectional, view schematically showing a surface laminated structure of an exemplary embodiment of the medical device according to the present disclosure (hereinunder also abbreviated as "medical device"). FIG. 2 is a partial sectional view schematically showing another example of the surface laminated structure according to a further embodiment of the disclosure.

As illustrated in FIG. 1 and FIG. 2, a medical device 10, 10' is provided with a base layer 1 and lubrication layers 2 containing a block copolymer which are provided on at least a part of t e base layer 1 (in FIGS. 1 and 2, an example in which the lubrication layers 2 are provided throughout the surfaces (on the entire surfaces) of the base layer 1 in the drawings) is illustrated. Incidentally, in FIG. 1 and FIG. 2, the lubrication layer 2 is formed on both of the two opposing surfaces of the base layer 1. However, the disclosure is not limited to the illustrated embodiments, and any modification, such as a modification where the lubrication layer 2 is formed on one surface alone of the base layer 1 or a modification where the lubrication layer(s) 2 is(are) formed on a part of one surface alone or both, of the two opposing surfaces of the base layer 1, may be applicable and within the scope of the disclosure.

The base layer for use in the exemplary embodiments may be formed of any material, and the material is not particularly limited. Specific examples of the material forming the base layer 1 include a metal material, a polymer material, and a ceramic. Here, as for the base layer 1, the entire base layer 1 may be formed of any one of the above materials. The base layer 1 may have a multilayer structure in which multiple layers of different materials are laminated, or a structure in which members formed of different materials for different parts of the medical device are joined together. Alternatively, as shown in FIG. 2, the base layer 1 may have a structure in which a surface of a base layer core portion 1a formed of any one of the above materials is coated with another one of the above materials by an appropriate method to form a base surface layer 1b. As an example of the latter case, a structure in which a surface of the base layer core portion 1a formed of a polymer material or the like is coated with a metal material by an appropriate method (a conventionally known method such as plating, metal deposition, and spattering) to form the base surface layer 1b; a structure in which a surface of the base layer core portion 1a formed of a hard reinforced material, such as a metal material and a ceramic material, is coated with a polymer material which is softer than the reinforced material such as a metal material by an appropriate method (a conventionally known method, such as immersion (dipping), atomization (spraying), coating and printing), or a reinforced material for forming the base layer core portion 1a and a polymer material are combined into a composite to form the base surface layer 1b; or the like may be provided. The base layer core portion 1a may also have a multilayer structure in which multiple layers of different materials are laminated, or a structure in which members formed of different materials for different parts of the medical device are joined together. Alternately another middle layer (not shown) may be formed between the base layer core portion 1a and the base surface layer 1b. Furthermore, the base surface layer 1b may also have a multilayer structure in which multiple layers of different materials are laminated, or a structure in which members formed of different materials for different parts of the medical device are joined together.

Among the materials for forming the base layer 1, the metal material is not particularly limited and a metal material that is generally used for a medical device, such as a catheter, a guidewire, and an indwelling needle may be used. Specific examples thereof include various stainless steels, such as SUS304, SUS316, SUS316L, SUS420J2, and SUS630, gold, platinum, silver, copper, nickel, cobalt, titanium, iron, aluminum, tin, and various alloys, such as a nickel-titanium alloy, a nickel-cobalt alloy, a cobalt-chromium alloy, and a zinc-tungsten alloy. One of these materials may be used alone or two or more thereof may be used in combination. As the metal material for base layer 1, an optimal metal material for the base layer may be appropriately selected depending upon the purpose of use for a catheter, a guidewire, an indwelling needle, or the like.

Among the materials for forming the base layer 1, the polymer material is not particularly limited, and a polymer material that is generally used for a medical device, such as a catheter, a guidewire, and an indwelling needle may be used. Specific examples include a polyamide resin, a polyolefin resin, such as a polyethylene resin and a polypropylene resin, a modified polyolefin resin, a cyclic polyolefin resin, an epoxy resin, an urethane resin (polyurethane) a diallyl phthalate resin (an allyl resin), a polycarbonate resin, a fluoride resin, an amino resin (a urea resin, a melamine resin, a benzoguanamine resin), a polyester resin, a styrol resin, an acryl resin, a polyacetal resin, a vinyl acetate resin, a phenol resin, a vinyl chloride resin, a silicone resin (a silicon resin), a polyether resin, and a polyimide resin. One of these materials may be used alone or two or more thereof may be used together in mixture. Also, a copolymer of two or more monomers each composing any one of the above resins may be used. As the polymer material, an optimal polymer material for the base layer may be appropriately selected depending upon the purpose of use for a catheter, a guidewire, an indwelling needle, or the like.

The shape of the base layer is not particularly limited, and a shape of sheet, line (wire), tube, and the like is appropriately selected according to the use of the medical device.

The lubrication layer is supported on at least a part of the base layer. Here, the reason why the lubrication layer 2 is supported on at least a part of the base layer surface is that, in a medical device such as a catheter, a guidewire, or an indwelling needle, for example, all of the surface (the entire surface) of the medical device is not always required to have lubricity when being wetted, and the lubrication layer is required to be supported on only the portion of the surface that is required to have lubricity when being wetted (which is a part of the base layer in some cases and all of the base layer in other cases). For this reason, as described above, an embodiment where the lubrication layer is formed so as to cover all of the two opposing surface of the base layer as shown in FIGS. 1 and 2; an embodiment where the lubrication layer is formed so as to cover all of one surface alone of the base layer; an embodiment where the lubrication layer is formed so as to cover only portions of the two opposing surfaces of the base layer in the same manner or in different manners; an embodiment where the lubrication layer is formed so as to cover a part of one surface alone of the base layer; and the like, are encompassed by the disclosure here. Incidentally, as used herein, the term "support" means a state where the lubrication layer is fixed in a state where the lubrication layer is not easily released from the base layer surface.

The lubrication layer contains the block copolymer (A) and the polymer (B). In the lubrication layer, the composition of the block copolymer (A) and the polymer (B) is, such that the block copolymer (A) is present in a proportion of 20 to 80% by weight relative to the total weight of the block copolymer (A) and the polymer (B), or in other words, the polymer (B) is present in a proportion of 80 to 20% by weight relative to the total weight of the block copolymer (A) and the polymer (B). When the mixing ratio of the block copolymer (A) is less than 20% by weight (the mixing ratio of the polymer (B) is more than 80% by weight), the constituting unit (A-1) derived from the block copolymer (A) cannot form a sufficient mesh structure (network), the strength of the lubrication layer is insufficient, and the lubrication layer is separated from the base layer (see Comparative Example 2 described later). In contrast, when the mixing ratio of the block copolymer (A) is more than 80% by weight (the mixing ratio of the polymer (B) is less than 20% by weight), the amount of the polymer (B) is too small and the effects of enhancing the lubricity and swellability of the constituting unit (A-2') derived from the polymer (B) are not sufficiently achieved (see Comparative Example 1 described later). In view of the effects of enhancing the lubricity, swellability, and durability, the block copolymer (A) is preferably present in a proportion of 20% by weight or more and less than 50% by weight, and more preferably 20 to 40% by weight, relative to the total weight of the block copolymer (A) and the polymer (B).

The content of the block copolymer (A) and the polymer (B) in the lubrication layer can be measured by a known method. In the present disclosure, the content of the block copolymer (A) and the polymer (B) in the lubrication layer is a value measured by a method described below.

For each medical device (hereinunder also simply referred to as "sample"), in accordance with the following method, the weights of the block copolymer (A) and the polymer (B) per unit area of the lubrication layer (the lubrication-coated part) are calculated.

Specifically, the medical device whose weight (W0(g)) is previously measured is heated and refluxed in distilled water at 100° C. for 3 hours to extract the polymer (B). After being heated and refluxed for a prescribed time period, the medical device is taken out and dried at 100° C. for 1 hour, then the weight (W1(g)) is measured, the loss in the weight between before and after the extraction (WB(g)) [=(W0(g))−(W1(g))] is calculated, and the weight loss (WB(g)) is taken as the weight of the polymer (B) contained in the lubrication layer. Further, the concentrated residue of the extracted liquid after the heating and refluxing is subjected to Nuclear Magnetic Resonance (NMR) analysis and confirmed to be the polymer (B).

Next, the thus-dried, medical device is further heated and refluxed in 2N hydrochloric acid (2N HCl) at 100° C. for 1 hour to extract the block copolymer (A) from the lubrication layer. (In the case of HCL, 2N is the same as 2M as there is only one H+ ion in the acid.) Thereafter, the medical device is taken out and dried at 100° C. for 1 hour, and then the weight (W2(g)) is measured. The weight loss between before and after the 2N HCL treatment of the medical device (WA(g)) [=(W1(g))−(W2(g))] is calculated, and the weight loss (WA(g) is taken as the weight of the block copolymer (A) contained in the lubrication layer. Further, the concentrated residue of the treated liquid after the heating and refluxing is subjected to IR analysis and confirmed to be the block copolymer (A).

Based on the weight loss ((WA(g) and WB(g)) measured in this manner, the content of the block copolymer (% by weight) is calculated according to the following formula.

$$\text{Content of block copolymer }(A)(\% \text{ by weight}) = \frac{W_A(g)}{W_A(g) + W_B(g)} \times 100 \quad \text{[Equation 1]}$$

The lubrication layer contains the block copolymer (A) and the polymer (B) as primary components. The lubrication layer may contain another component in addition to the block copolymer (A) and the polymer (B). Here, the other component is not particularly limited. In cases where the medical device is one intended to be inserted into a body cavity or a lumen, such as a catheter, examples thereof include drugs (bioactive substances), such as an anticancer agent, an immunosuppressive agent, an antibiotic, an antirheumatic drug, an antithrombotic drug, an HMG-CoA reductase inhibitor, an ACE inhibitor, a calcium antagonist, an antilipemic drug, an integrin inhibiting drug, an antiallergic agent, an antioxidant, a GPIIbIIIa antagonistic drug, retinoid, flavonoid, carotenoid, a lipid improving drug, a DNA synthesis inhibitor, a tyrosine kinase inhibitor, an antiplatelet drug, a vascular smooth muscle growth inhibiting drug, an anti-inflammatory drug, a living body-derived material, interferon, and an NO production promotor. Here, the addition amount of the other component is not particularly limited, and a commonly-used amount is similarly applied. Finally, the addition amount of the other component is appropriately selected in consideration of the severity of the disease to which the invention is applied, body weight of the patient, and the like.

The reactive monomer composing the block copolymer (A) has an epoxy group as a reactive group. By introducing the constituting unit (A-1) derived from such a reactive monomer into the block copolymer (A), the block copolymer (A) is crosslinked or polymerized via the epoxy groups to form a mesh structure. For this reason, the strength of the lubrication layer can be enhanced. Thus, the shape of the medical device in the present disclosure can be maintained successfully even after sliding. In addition, the lubrication layer can be strongly connected (fixed) to the base layer via the epoxy groups, and separation from the base layer can be suppressed or prevented. Thus, the medical device according to the disclosure herein is excellent in durability. The block copolymer (A) having the constituting unit (A-1) derived from a monomer having an epoxy group shows a mild reaction rate (an appropriate rate) when being reacted by a heating and drying operation (heating and drying treatment) and the like. For this reason, when the epoxy groups are subjected to a crosslinking reaction through a heating, drying, or other operation, the reaction rate is mild to the extent that immediate reaction resulting in gelation and solidification resulting in increase of crosslinking density of the coating layer (lubrication layer) which leads to deterioration of lubricity, lubricity maintaining effect, and blood compatibility are suppressed or controlled (an appropriate rate), and therefore the handling is easy.

Further, formation of the mesh structure (network) by the constituting unit (A-1) composing the block copolymer (A) can be confirmed by a known method. The formation of the mesh structure (network) is confirmed in this description by disappearance of the epoxy group and formation of an ether bond in ATR-IR (Attenuated Total Reflection-Infrared).

In addition the hydrophilic monomer (constituting unit (A-2)) composing the block copolymer (A) imparts the swellability with solvent, and in turn, the lubricity (surface lubricity) under contact with a body fluid or an aqueous solvent. For this reason, with the medical device according to the disclosure herein, friction under contact with a lumen wall such as a vascular wall can be reduced.

The hydrophilic monomer (constituting unit (A-2')) composing the polymer (B), like the hydrophilic monomer composing the block copolymer (A), also imparts the swellability with solvent, and in turn, the lubricity (surface lubricity) under contact with a body fluid or an aqueous solvent. Hence, the medical device of the present disclosure can reduce friction under contact with a lumen wall such as vascular wall. In addition, at least a part of the constituting unit (A-2') composing the polymer (B) enters the inside (void) of the mesh structure (network) formed by the constituting unit (A-1) composing the block copolymer (A), or entangles (is integrated) with each of the constituting units (A-1) and (A-2) of the block copolymer (A). For this reason, even under friction in contact with a lumen wall such as a vascular wall, the medical device according to the disclosure here is excellent in durability since elimination of the polymer (B) from the lubrication layer is effectively suppressed or prevented. Further, while entanglement (integration) of the polymer (B) with the block copolymer (A) is difficult to confirm by an analysis and the like it can be inferred from durability (sliding durability). Specifically, when a difference between the initial sliding resistance and the sliding resistance after test [=(the initial sliding resistance (gf))-(the sliding resistance after test (gf))] measured in Examples described later is 10 gf or less, it is determined that the polymer (B) sufficiently enters the inside (void) of the mesh structure (network) formed by the constituting unit (A-1) composing the block copolymer (A), and/or is sufficiently entangled with each constituting unit of the block copolymer (A). In view of the effect of further enhancing the lubricity and swellablity, the difference between the initial sliding resistance and the sliding resistance after test [=(the initial sliding resistance (gf))-(the sliding resistance after test (gf))] is preferably 0 to 6 gf, and more preferably 0 to 4 gf.

Here, the reactive monomer composing the block copolymer (A) is not particularly limited as long as it has an epoxy group. Specific examples include glycidyl acrylate, glycidyl methacrylate (GMA), 3,4-epoxycyclohexylmethyl acrylate, 3,4-epoxycyclohexylmethyl methacrylate, β-methylglycidyl methacrylate, and allyl glycidyl ether. Among them, in view of enhancing ease of formation of the mesh structure and ease of production, glycidyl (meth)acrylate is preferred. One of the reactive monomer may be used alone, or two or more thereof may be used in combination.

In addition, the hydrophilic monomers composing the block copolymer (A) and the polymer (B) are selected from the group consisting of acrylamide and an acrylamide derivative. The acrylamide derivative is not particularly limited as long as it can impart lubricity by coming into contact with a body fluid or an aqueous solvent. Specific examples include N-methylacrylamide, N,N-dimethylacrylamide, and acrylamide. Among them, N,N-dimethylacrylamide is preferred in view of enhancement of lubricity and safety of the monomer. In the block copolymer (A), one of the hydrophilic monomers may be used alone or two or more thereof may be used in combination. Similarly, in the polymer (B), one of the hydrophilic monomers may be used alone or two or more thereof may be used in combination. In addition, the hydrophilic monomer composing the block copolymer (A) and the hydrophilic monomer composing the polymer (B) may be the same as or different from each other. In view of affinity between the block copolymer (A) and the polymer (B), and the like, the hydrophilic monomer composing the block copolymer (A) and the hydrophilic monomer composing the polymer (B) are preferably the same.

The block copolymer (A) according to the disclosure herein contains the constituting unit (A-1) and the constituting unit (A-2). Here, the ratio of the constituting unit (A-1) and the constituting unit (A-2) is not particularly limited as long as the above effects are achieved. In view of the good lubricity, lubricity maintaining effect, strength of the coating layer, and connectivity with the base layer, the ratio of the constituting unit (A-1) and the constituting unit (A-2) (the molar ratio of the constituting unit (A-1): the constituting unit (A-2)) is preferably 1:2 to 100, and more preferably 1:2 to 50. In the above range, the lubrication layer can sufficiently exhibit the lubricity and lubricity maintaining effect owing to the constituting unit (A-2), and the sufficient strength of the coating layer, connectivity with the base layer, and durability can be exhibited owing to the constituting unit (A-1).

The method of producing the block copolymer (A) according to the present disclosure is not particularly limited, and, for example, a conventionally known polymerization method, such as a living radical polymerization method, a polymerization method using a macro initiator, or a polycondensation method, can be applied to produce the block copolymer (A). Among them, in terms of ease of controlling the molecular weights and the molecular weight distribution of the constituting unit (moiety) derived from the hydrophilic monomer and the constituting unit (moiety) derived from the reactive monomer, a living radical polymerization method or a polymerization method using a macro initiator is preferably used. The living radical polymerization method is not particularly limited, and, for example, methods described in JP-A-H-11-263819 JP-A-2002-145971, JP-A-2006-316169, etc., and an atom transfer radical polymerization (ATRP) method, etc. can be applied as it is or with appropriate modification. In the polymerization method using a macro initiator, for example, a macro initiator including a hydrophobic moiety having a reactive functional group and a radical polymerizable group such as a peroxide group are produced, and then the macro initiator is polymerized with a monomer for forming a hydrophilic moiety, whereby the block copolymer (A) having a hydrophilic moiety and a hydrophobic moiety can be produced.

In polymerization of the block copolymer (A) or the polymer (B), a known method, such as bulk polymerization, suspension polymerization, emulsion polymerization, and solution polymerization, may be used. Specifically, in production of the block copolymer (A), a method in which the reactive monomer and the hydrophilic monomer are heated with a polymerization initiator while stirring in a polymerization solvent to copolymerize the monomers may be used. In production of the polymer (B), a method in which the hydrophilic monomers are heated with a polymerization initiator while stirring in a polymerization solvent to copolymerize the monomers may be used. Here, the polymerization initiator is not particularly limited, and a known one may be used. Preferably, in view of excellent polymerization stability, a radical polymerization initiator is preferred. Specific examples include a persulfate salt, such as potassium persulfate (KPS), sodium persulfate, and ammonium persulfate; a peroxide, such as hydrogen peroxide, t-butyl peroxide, and methyl ethyl ketone peroxide; and an azo compound, such as azobisisobutyronitrile (AIBN), 2,2'-azobis(2-methylbutyronitrile), and azobiscyanovaleric acid. In addition, for example, the radical polymerization initiator may be combined with a reductant, such as sodium sulfite, sodium hydrogen sulfite, and ascorbic acid, and used as a redox type initiator. The amount of the polymerization initiator incorporated is preferably 0.0001 to 1% by mole relative to the total amount of the monomers.

The polymerization solvent is not particularly limited, but, for example, an aliphatic-type organic solvent, such as n-hexane, n-heptane, n-octane, n-decane, cyclohexane, methylcyclohexane, and a liquid paraffin; an ether-type solvent, such as tetrahydrofuran and dioxane; an aromatic-type organic solvent, such as toluene and xylene; a halogen-type organic solvent, such as 1,2-dichloroethane and chlorobenzene; and a polar aprotic organic solvent, such as N,N-dimethylformamide and dimethylsulfoxide, may be used. Further, the solvents may be used alone or in mixture of two or more thereof. In the concentration of the monomers in the polymerization solvent (for the block copolymer (A), the total concentration of the hydrophilic monomer and the reactive monomer, and for the polymer (B), the total concentration of the hydrophilic monomer) is preferably 5 to 90% by weight, more preferably 8 to 80% by weight, and particularly preferably 10 to 50% by weight.

In the polymerization described above, the conditions for polymerization are also not particularly limited as long as the (co)polymerization proceeds. For example, it is preferred that the temperature for polymerization is preferably 30 to 150° C., and more preferably 40 to 100° C. In addition, the time for polymerzation is preferably 30 minutes to 30 hours, and more preferably 3 to 24 hours.

Furthermore, in the (co)polymerization as needed, a chain transfer agent, a polymerization rate regulator, a surfactant, a water-soluble polymer, a water-soluble inorganic compound (an alkali metal salt, an alkali metal hydroxide, a polyvalent metal salt, a non-reducible alkali metal salt pH buffer, etc.), an inorganic acid, an inorganic acid salt, an organic acid, an organic acid salt, and other additives may be appropriately used.

The block copolymer (A) and the polymer (B) after the (co)polymerization are preferably purified by a common purification method, such as reprecipitation method, a dialysis method, an ultrafiltration method, or an extraction method.

The lubrication layer is formed on the base layer by using the block copolymer (A) and the polymer (B) produced in the foregoing manner.

Method for Forming Lubrication Layer

In the present disclosure, the method for forming the lubrication layer on the base layer is not particularly limited as long as the block copolymer (A) and the polymer (B) are used in the specific mixing ratio, and a known method can be applied as it is or with an appropriate modification. For example, it, is preferred that the block copolymer (A) and the polymer (B) are dissolved in a solvent to prepare a mixture liquid, the base layer is coated with the mixture liquid, and then the block copolymer (A) is crosslinked or polymerized in the absence of a catalyst, thereby forming a mesh structure on the base layer. That is, a second aspect of the disclosure provides a method for producing the medical device according to the disclosure above, including dissolving the block copolymer (A) and the polymer (B) in a solvent to prepare a mixture liquid, coating the base layer with the mixture liquid, and then crosslinking or polymerizing the block copolymer (A) in the absence of a catalyst, thereby forming the mesh structure on the base layer. Through the method, lubricity and durability can be imparted to a medical device surface. In addition, according to the method, since the block copolymer (A) is crosslinked or polymerized in the absence of a catalyst, the crosslinking/polymerization can be appropriately controlled. For this reason, since the mesh structure (network) by the block copolymer (A) can be appropriately formed, it is possible to sufficiently ensure the void that the polymer (B) enters while ensuring the strength of the lubrication layer.

A preferred method for producing the medical device of the disclosure will be described hereinbelow, by way of example, but the disclosure is not to be limited to the following method.

In the method described above, the solvent used for dissolving the block copolymer (A) and the polymer (B) according to the present disclosure is not particularly limited as long as it can dissolve the block copolymer (A) and the polymer (B) according to the present disclosure. Specific examples include, but are, not limited to: water; an alcohol, such as methanol, ethanol, isopropanol, and ethylene glycol; a ketone, such as acetone, methyl ethyl ketone, and cyclohexanone; an ester, such as ethyl acetate; a halide, such as chloroform; an olefin, such as hexane; an ether, such as tetrahydrofuran and butyl ether; an aromatic compound, such as benzene and toluene an amide, such as N,N-dimethylformamide (DMF); and a sulfoxide, such as dimethylsulfoxide. One of the solvents may be used alone or two or more thereof may be used in combination.

The concentrations of the block copolymer (A) and the polymer (B) in the mixture liquid are not particularly limited as long as the block copolymer (A) and the polymer (B) are contained at the mixing ratio according to the disclosure here. From the viewpoint that the applicability and the desired effects (lubricity and durability) can be achieved, the total concentration of the block copolymer (A) and the polymer (B) in the mixture liquid is 0.01 to 20% by weight, more preferably 0.05 to 15% by weight, and further preferably 0.1 to 10% by weight. When the concentration is in the above range, the lubricity and durability of the resulting lubrication layer can be sufficiently exhibited. Since a uniform lubrication layer having a desired thickness can be easily obtained by one time coating, such a concentration is preferred also in terms of operability (for example, ease of coating) and production efficiency. However, a concentration out of the range is sufficiently applicable unless the concentration affects the functions and effects of the present invention.

The method for forming a coating of (applying) the mixture liquid on the base layer surface is not particularly limited, and a conventionally known method, such as a coating and printing method, an immersion method (dipping method dip-coating method), an atomization method (spraying method), a spin-coating method, and a mixture liquid impregnation sponge-coating method, can be applied. Among these, an immersion method (dipping method, dip-coating method) is preferably used.

Further, in cases where the lubrication layer is formed on a thin and narrow inner surface of a catheter a guidewire, an injection needle, and the like, the base layer may be immersed in the mixture liquid and the pressure in the system may be reduced to effect defoaming. By effecting defoaming under a reduced pressure, it is possible to allow the solution to quickly penetrate into the thin and narrow inner surface to promote the formation of the lubrication layer.

In addition in cases where the lubrication layer is to be formed on only a part of the base layer, only the part of the base layer is immersed in the mixture liquid to coat the part of the base layer with the mixture liquid, whereby the lubrication layer can be formed on the desired surface portion of the base layer.

When it is difficult to immerse only a part of the base layer in the mixture liquid, the surface portion of the base layer on which the lubrication layer is not to be formed can first be protected (coated, or the like) with an appropriate removable (detachable) member or material and, the base layer then is immersed in the mixture liquid to coat the base layer with the mixture liquid. Thereafter, the protection member (material) on the surface portion of the base layer on which the lubrication layer is not to be formed is removed, and then a reaction is effected by a heating treatment or the like, whereby the lubrication layer can be formed on the desired surface portion of the base layer. However, the disclosure herein is by no means limited to the formation methods mentioned above, and the lubrication layer may be formed by appropriately using a conventionally known method. For example, when it is difficult to immerse only a part of the base layer in the mixture solution, instead of the immersion method, another coating technique (for example, a method in which a mixture liquid is applied on a prescribed surface portion of a medical device using an application apparatus, such as a spraying apparatus, a bar coater, a die coater, a reverse coater, a comma coater, a gravure coater, a spray coater, and a doctor knife) may be applied. Incidentally, in cases where both the outer surface and the inner surface of a cylindrical device are required to have a lubrication layer for the reason of the structure of a medical device, the immersion method (dipping method) is preferably used since both the outer surface and the inner surface are simultaneously coated.

After immersing the base layer in a mixture liquid containing the block copolymer (A) and the polymer (B) in the specific mixing ratio in this manner, the base layer is taken out of the mixture liquid and subjected to a drying treatment. Here, the conditions for drying the mixture liquid (temperature, time, and the like) are not particularly limited as long as the lubrication layer containing the block copolymer (A) and the polymer (B) can be formed on the base layer. Specifically, the temperature for drying is preferably 20 to 200° C. and more preferably 50 to 150° C. In addition, the time for drying is preferably 30 minutes to 30 hours, and more preferably 1 to 20 hours. Under the conditions, the lubrication layer (coating layer) containing the block copolymer (A) and the polymer (B) according to the present disclosure is formed on the base layer surface, and a crosslinking reaction occurs via the epoxy groups in the block copolymer (A) in the lubrication layer, whereby the lubrication layer having high strength that is not easily separated from the base layer can be formed. In addition, by the drying step as mentioned above, connection (fixing) with the base layer occurs, and separation from the base layer is effectively suppressed or prevented.

In addition, the pressure condition in drying is by no means limited, and drying may be performed under normal pressure (atmospheric pressure) or may be performed, under an increased or reduced pressure.

As a drying means (apparatus), for example, an oven, a vacuum dryer, or the like may be used. In cases of natural drying, no particular drying means (apparatus) is required.

According to the foregoing method, the lubrication layer (coating layer) containing the block copolymer (A) and the polymer (B) according to the disclosure is formed on the base layer surface, and then the epoxy groups are cross-linked, whereby a strong lubrication coating layer that is not easily separated from the base layer can be formed. In addition, in the medical device according to the disclosure herein, a coating layer formed by the block copolymer (A) according to the present disclosure is formed on a surface thereof. For this reason, the medical device according to the present disclosure can exhibit excellent lubricity and lubricity maintaining effect.

The medical device according to the disclosure herein is a device used in contact with a body fluid or blood, and a surface thereof has lubricity in an aqueous liquid, such as a body fluid and a physiological saline, making it possible to enhance operability and reduce damage in tissue and mucosa. Specific examples include a catheter, a guidewire, and an indwelling needle that are used in a blood vessel, but in addition, the following medical devices may be exemplified.

(a) A catheter that is inserted or allowed to indwell orally or nasally in a digestive organ, such as a stomach tube catheter, a nutritional catheter, and a tubal feeding tube.

A catheter that is inserted or allowed to indwell orally or nasally in a respiratory tract or a trachea, such as an oxygen catheter, an oxygen cannula, a tube and cuff of an endotracheal tube, a tube and cuff of a tracheostomy tube, and an tracheal aspiration catheter.

A catheter that is inserted or allowed to indwell in a urethra or a ureter, such as a urethral catheter, a urine guide catheter, and a catheter and a balloon of a urethral balloon catheter.

(d) A catheter that is inserted or allowed to indwell in a body cavity, an organ, and a tissue of various kinds, such as a suction catheter, a drainage catheter and a rectum catheter.

(e) A catheter that is inserted or allowed to indwell in a blood vessel, such as an indwelling needle, an IVH catheter, a thermodilution catheter, an angiographic catheter, a vasodilating catheter, dilator and an introducer, or a guidewire and a stylet for such a catheter.

(f) An artificial trachea, an artificial bronchus, and the like.

(g) a medical device for extracorporeal circulation treatment (an artificial lung, an artificial heart, an artificial kidney, and the like) or a circuit therefor.

Advantageous effects of the present disclosure will be described through the following Examples and Comparative Examples. However, the technical scope of the present invention is not limited only to the following Examples. Incidentally, in the following Examples, unless otherwise specified, the operation was conducted at a room temperature (25° C.). In addition, unless otherwise specified, "%" and "parts" mean "20% by weight" and "parts by weight", respectively.

Synthetic Example 1: Synthesis of Block Copolymer (A1)

After 29.7 g of triethylene glycol was added dropwise into 72.3 g of adipic acid dichloride at 50° C., hydrochloric acid was removed under reduced pressure at 50° C. for 3 hour to give an oligoester. Next, 4.5 g of methyl ethyl ketone was added to 22.5 g of the resulting oligoester, and the mixture was added drop wise into a solution of 5 g of sodium hydroxide, 6.93 of 31% hydrogen peroxide, 0.44 g of dioctyl phosphate as a surfactant, and 120 g of water to effect a reaction at −5° C. for 20 minutes. The resulting product was repeatedly washed with water and methanol, and then dried to give a polyperoxide (PPO) having plural peroxide groups in a molecule.

Next, 0.5 g of the PPO and 9.5 g of glycidyl methacrylate (GMA) were polymerized in 30 g of benzene as a solvent while stirring at 80° C. for 2 hours under reduced pressure. The resulting reaction product after the polymerization was reprecipitated from diethyl ether to give a poly(glycidyl methacrylate) (PPO-GMA) having plural peroxide groups in a molecule.

Subsequently, 1.0 g of the resulting PPO-GMA (corresponding to 7 mmol of GMA) was mixed with 9.0 g of dimethylacrylamide (DMAA) and 90 g of dimethyl sulfoxide as a solvent, and the mixture was reacted at 80° C. for 18 hours. The resulting reaction product after the reaction was reprecipitated from hexane and collected to give a block copolymer (A1) (DMAA:GMA=14:1 (molar ratio)) that has an epoxy group in the molecule and exhibits lubricity when being wetted. The thus-obtained block copolymer (A1) was analyzed by NMR and IR, and thus it was confirmed that an epoxy group existed in the molecule.

Synthetic Example 2: Synthesis of Polymer (B1)

In a reaction container that can be sealed, 10 g of dimethylacrylamide (DMAA) was dissolved in 90 g of dimethyl sulfoxide as a solvent, and 0.05 g of azobisisobutyronitrile was added as an initiator to the solution to effect a reaction at 80° C. for 18 hours under reduced pressure. The reaction product was purified through reprecipitation from hexane to give a polymer (B1). The thus-obtained polymer (B1) was analyzed by NMR and IR, and thus the polymer was confirmed to be a homopolymer of dimethylacrylamide.

Synthetic Example 3: Synthesis of Polymer (C1)

In a reaction container that can be sealed, 10 g of glycidyl methacrylate (GMA) was dissolved in 90 g of dimethyl sulfoxide as a solvent, and 0.05 g of azobisisobutyronitrile was added as an initiator to the solution to effect a reaction at 80° C. for 18 hours under reduce pressure. The reaction product was purified by reprecipitation from hexane to give a polymer (C1). The thus-obtained polymer (C1) was analyzed by NMR and IR, and thus the polymer was confirmed to be a homopolymer of glycidyl methacrylate.

Example 1

The block copolymer (A1) obtained in Synthetic Example 1 and the polymer (B1) obtained in Synthetic Example 2 were mixed in 40:60 (by weight), and the mixture was dissolved in tetrahydrofuran (THF) so as to give a concentration (total concentration) of 3% by weight to prepare a mixture solution (1). A tube made of a polyurethane having an outer diameter of 5 Fr (1.65 mm diameter) was immersed in this mixture solution (1), and dried to effect a reaction in an oven of 60° C. for 18 hours to produce a coated tube (1) having formed on a surface thereof a coating layer (lubrication layer) that contains the block copolymer (A1) and the polymer (B1). When the coated tube (1) was immersed in a physiological saline and rubbed with a finger, it was confirmed that the surface was more slippery and had lower friction as compared with an untreated tube.

Furthermore, when the coated tube (1) was subjected to a surface analysis by ATR-IR, no peak of an epoxy group was recognized and a peak of an ether bond was recognized, whereby crosslinking of epoxy groups was confirmed.

The coated tube (1) was also evaluated for surface lubricity and durability (sliding durability), and swellability according to test methods described hereinbelow. The results are shown in Table 1.

Example 2

A coated tube (2) was produced according to the same method as in Example 1, except that the mixing ratio of the block copolymer (A1) and the polymer (B1) in Example 1 was changed to 80:20 (by weight). When the coated tube (2) was immersed in a physiological saline and rubbed with a finger, it was confirmed that the surface was more slippery and had lower friction as compared with an untreated tube.

Furthermore, when the coated tube (2) was subjected to a surface analysis by ATR-IR, no peak of an epoxy group was recognized and a peak of an ether bond was recognized, whereby crosslinking of epoxy groups was confirmed.

The coated tube (2) was also evaluated for surface lubricity and durability (sliding durability), and swellability according to test methods described hereinbelow. The results are shown in Table 1.

Example 3

A coated tube (3) was produced according to the same method as in Example 1, except that the mixing ratio of the block copolymer (A1) and the polymer (B1) in Example 1 was changed to 20:80 (by weight). When the coated tube (3) was immersed in a physiological saline and rubbed with a finger, it was confirmed that the surface was more slippery and had lower friction than an untreated tube.

Furthermore, when the coated tube (3) was subjected to a surface analysis by ATR-IR, no peak of an epoxy group was recognized and a peak of an ether bond was recognized, whereby crosslinking of epoxy groups was confirmed.

The coated tube (3) was also evaluated for surface lubricity and durability (sliding durability), and swellability according to test methods described hereinbelow. The results are shown in Table 1.

Comparative Example 1

A coated tube (4) was produced according to the same method as in Example 1, except that the mixing ratio of the block copolymer (A1) and the polymer (B1) in Example 1 was changed to 90:10 (by weight). When the coated tube (4) was immersed in a physiological saline and rubbed with a finger, the surface was more slippery as compared with an untreated tube, but had lower lubricity than the surfaces of the coated tubes (1) to (3).

The coated tube (4) was also evaluated for surface lubricity and durability (sliding durability), and swellability according to test methods described hereinbelow. The results are shown in Table 1.

Comparative Example 2

A coated tube (5) was produced according to the same method as in Example 1, except that the mixing ratio of the block copolymer (A1) and the polymer (B1) in Example 1 was changed to 10:90 (by weight). When the coated tube (5) was immersed in a physiological saline and rubbed with a finger, separation easily occurs and the surface had lower durability.

The coated tube (5) was also evaluated for swellability according to test method described hereinbelow. The result is shown in Table 1. In the coated tube (5), the coating layer was easily separated, and the surface lubricity and the durability (sliding durability) were not able to be measured.

Comparative Example 3

The polymer (B1) obtained in Synthetic Example 2 described above and the polymer (C1) obtained in Synthetic Example 3 described above were mixed in a mixing ratio of 50:50 (by weight), and the mixture was dissolved in tetrahydrofuran (THF) so as to give a concentration (total concentration) of 3% by weight, whereby a mixture solution (2) s prepared.

In Example 1, a coated tube (6) was produced according to the same method as in Example 1 except that the mixture solution (2) prepared above was used in place of the mixture solution (1). When the coated tube (6) was immersed in a physiological saline and rubbed with a finger, the surface was more slippery as compared with an untreated tube but had lower lubricity than the surfaces of the coated tubes (1) to (3).

The coated tube (6) was also evaluated for surface lubricity and durability (sliding durability), and swellability according to test methods described hereinbelow. The results are shown in Table 1.

Experiment: Evaluation of Performance

The coated tubes (1) to (6) produced in Examples 1 to 3 and Comparative Examples 1 to 3 described above were evaluated for surface lubricity and durability (sliding durability), and swellability by the test method described below. The results are shown in Table 1.

[Evaluation of Surface Lubricity and Durability (Sliding Durability)]

Figure 3:
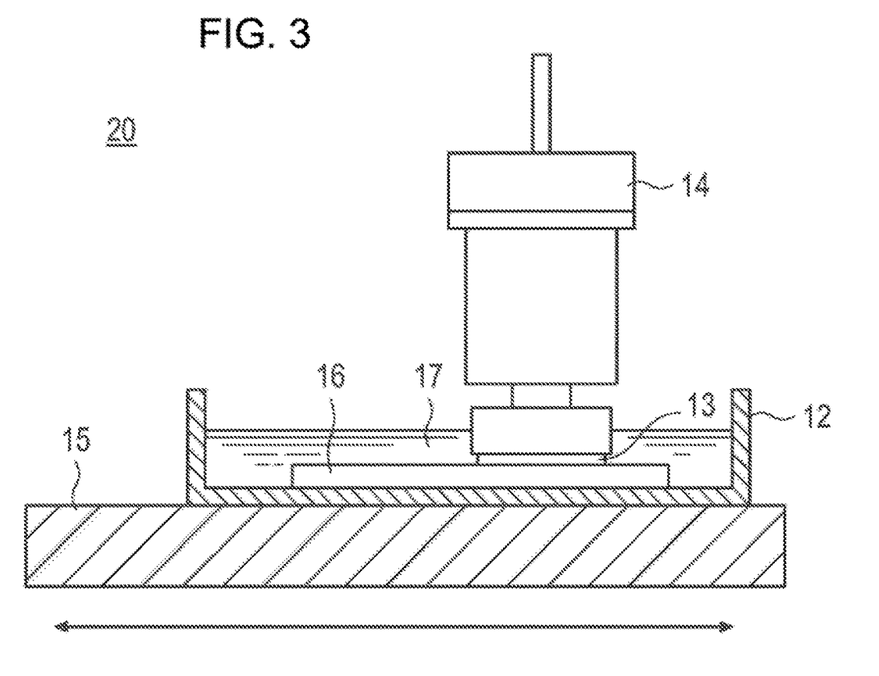
FIG. 3 is a schematic diagram of a tester (friction tester) for evaluating surface lubricity and durability used in the Examples and Comparative Examples according to the disclosure.

For each medical device (hereinunder also simply referred to as "sample"), a sliding resistance (gf) of the coating layer (lubrication layer) was measured according to a method described below using a friction tester (manufactured by Trinity-Lab, Inc., Handy Tribo Master TL201) 20 as shown in FIG. 3 to evaluate the lubricity.

Specifically, each sample 16 was fixed in a petri dish 12 and immersed in water 17 having such a depth that the entire sample 16 can be immersed. The petri dish 12 was placed on a moving table 15 of the friction tester 20 shown in FIG. 3. A cylindrical SEBS terminal (φ=7 mm) 13 was brought into contact with the sample 16, and a load 14 of 200 g was exerted on the terminal. At settings of a speed of 16.7 mm/sec and a moving distance of 20 mm the moving table 15 was subjected to two horizontal reciprocating movements to measure the sliding resistance (the initial sliding resistance in Table 1) (gf). The measured value was taken as an initial surface lubricity value. In addition, under the same conditions as above, the sliding resistance (the sliding resistance after test in Table 1) (gf) after 50 horizontal reciprocating movements was taken as a sliding durability (surface lubricity maintaining effect) value. Hence, the lower the sliding resistance (gf) value, the better the surface lubricity. In particular, an initial sliding resistance and a sliding resistance after test of less than 35 gf were considered as acceptable values.

Evaluation of Swellability

For each medical device (hereinunder also simply referred to as "sample"), the swelling degree (times) was measured according to a method described below to evaluate the swellability.

Specifically, the coating layer (lubrication layer) of each sample was immersed in water for 30 minutes to allow the sample to swell, and then the swelled coating layer was rubbed and separated with a metallic spatula and the weight (X1 (g)) was measured. The separated coating layer was dried at 100° C. for 1 hour, and the weight (X0 (g)) of the dried coating layer was measured. A value ((X1)/(X0)) obtained by dividing the weight (X1 (g)) in the swelled state by the weight (X0(g)) in the dried state was taken as the swelling degree (times).

TABLE 1

| | Block copolymer (A1) (wt %) | Polymer (B1) (wt %) | Initial sliding resistance (gf) | Sliding resistance after test (gf) | Swelling degree (times) |
|---|---|---|---|---|---|
| Example 1 | 40 | 60 | 11 | 11 | 35 |
| Example 2 | 80 | 20 | 28 | 28 | 19 |
| Example 3 | 20 | 80 | 10 | 10 | 38 |
| Comparative Example 1 | 90 | 10 | 35 | 35 | 10 |
| Comparative Example 2 | 10 | 90 | Not measurable due to separation | Not measurable due to separation | 40 |
| | Polymer (C1) (wt %) | Polymer (B1) (wt %) | Initial sliding resistance (gf) | Sliding resistance after test (gf) | Swelling degree (times) |
| Comparative Example 3 | 50 | 50 | 40 | 80 | 5 |

Block copolymer (A1) block copolymer of glycidyl methacrylate and dimethylacrylamide
Polymer (B1): homopolymer of dimethylacrylamide
Polymer (C1): homopolymer of glycidyl methacrylate It can be seen from the results of Table 1 above that the coated tubes (1) to (3) of the disclosure herein, as compared with the coated tubes (4) and (5) (Comparative Examples 1 and 2) in which the mixing ratio of the block copolymer (A1) and the polymer (B1) was out of the range according to the present disclosure, show significantly lower values of both the initial sliding resistance and the sliding resistance after test, and thus can exhibit superior surface lubricity and surface lubricity maintaining effect. It can also be seen that the coated tubes (1) and (3) of the disclosure show the swellability of an equal level to the tube (5) (Comparative Example 2) which contains a large amount of the polymer (B1) which is a homopolymer of dimethylacrylamide.

In addition to the foregoing, it is demonstrated that the coated tubes (1) to (3) according to the disclosure herein, as compared with the coated tube (6) (Comparative Example 3) which was coated with a mixture of equal amounts of the polymer (B1) which was a homopolymer of dimethylacrylamide and the polymer (C1) which was a homopolymer of glycidyl methacrylate, do not show a large difference in the initial surface lubricity but can be significantly enhanced in the durability (surface lubricity maintaining effect). It can also be seen that the coated tubes (1) to (3) of the present disclosure show higher swellability as compared with the coated tube (6) (Comparative Example 3). The reason why a large difference is not recognized in the initial surface lubricity between the coated tubes (1) to (3 of the present disclosure and the coated tube (6) is considered as follows: in the coated tube (6), the homopolymer of dimethylacrylamide (polymer (B1)) successfully enters the inside of the network formed by the homopolymer of glycidyl methacrylate (polymer (C1)). However, as the coating layer surface is rubbed, the homopolymer of dimethylacrylamide is easily removed from the network by the homopolymer of glycidyl methacrylate due to the friction. It is considered that the sliding resistance after test of the coated tube (6) is rapidly increased for this reason.

It is thus considered from the above results that the medical device according to the disclosure here, which includes a coating layer containing the block copolymer (A) and the polymer (B) in the specific proportions, is highly excellent in the surface lubricity and the sliding durability (surface lubricity maintaining effect).

The detailed description above describes features and aspects of an embodiment of a medical device and a method for producing the same. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A medical device comprising:
   a base layer; and
   a lubrication layer supported on at least a part of the base layer, wherein the lubrication layer contains a block copolymer (A) and a homopolymer (B), the block copolymer (A) being composed of a first constituting unit derived from a reactive monomer that has an epoxy group and a second constituting unit derived from at least one hydrophilic monomer selected from the group consisting of acrylamide and an acrylamide derivative, and the homopolymer (B) being composed of a constituting unit derived from at least one hydrophilic monomer selected from the group consisting of acrylamide and an acrylamide derivative,
   the block copolymer (A) is contained in a proportion of 20 to 80% by weight relative to the total weight of the block copolymer (A) and the homopolymer (B), and
   the block copolymer (A) is crosslinked or polymerized such that the block copolymer (A) forms a mesh structure.

2. The medical device according to claim 1, wherein the reactive monomer is at least one selected from the group consisting of glycidyl acrylate, glycidyl methacrylate (GMA), 3,4-epoxycyclohexylmethyl acrylate, 3,4-epoxycyclohexylmethyl methacrylate, β-methylglycidyl methacrylate, and allyl glycidyl ether.

3. The medical device according to claim 1, wherein the hydrophilic monomer composing the block copolymer (A) is at least one selected from the group consisting of N-methylacrylamide, N,N-dimethylacrylamide, and acrylamide.

4. The medical device according to claim 1, wherein the first constituting unit derived from a reactive monomer and the second constituting unit derived from a hydrophilic monomer that compose the block copolymer (A) are present in a molar ration of 1:2 to 100.

5. The medical device according to claim 4, wherein the first constituting unit derived from a reactive monomer and the second constituting unit derived from a hydrophilic monomer that compose the block copolymer (A) are present in a molar ration of 1:2 to 50.

6. The medical device according to claim 1, wherein the hydrophilic monomer that composes the homopolymer (B) is selected from the group consisting of N-methylacrylamide, N,N-dimethylacrylamide, and acrylamide.

7. The medical device according to claim 1, wherein the block copolymer (A) is contained in a proportion of more than 20% by weight and less than 50% by weight relative to the total weight of the block copolymer (A) and the homopolymer (B).

8. The medical device according to claim 7, wherein the block copolymer (A) is contained in a proportion of 20% to 40% by weight relative to the total weight of the block copolymer (A) and the homopolymer (B).

9. A method for producing the medical device as set forth in claim 1, comprising:
   dissolving the block copolymer (A) and the polymer (B) in a solvent to prepare a mixture liquid;
   coating at least a part of the base layer with the mixture liquid; and
   thereafter, crosslinking or polymerizing the block copolymer (A) in the absence of a catalyst to thereby form a mesh structure on the base layer.

10. The method according to claim 9, wherein the total concentration of the block copolymer (A) and the polymer (B) in the mixture liquid is 0.01 to 20% by weight.

11. The method according to claim 9, wherein the crosslinking or polymerizing are achieved by drying the coating film of the mixture liquid applied on the base layer at a temperature of 20 to 200° C. for 30 minutes to 30 hours.

12. The medical device according to claim 1, wherein homopolymer (B) is inside the mesh structure formed by block copolymer (A).

13. The medical device according to claim 1, wherein the base layer comprises a multilayer structure including a core portion and at least one surface layer.

14. The medical device according to claim 1, wherein the base layer comprises a metal material.

15. The medical device according to claim 1, wherein the lubrication layer is supported on an entirety of the base layer.

16. The medical device according to claim 1, wherein the lubrication layer further contains a drug.

17. A laminate structure comprising:
   a base layer; and
   a lubrication layer supported on at least a part of the base layer, wherein the lubrication layer contains a block copolymer (A) and a homopolymer (B), the block copolymer (A) being composed of a first constituting unit derived from a reactive monomer that has an epoxy group and a second constituting unit derived from at least one hydrophilic monomer selected from the group consisting of acrylamide and an acrylamide derivative, and the homopolymer (B) being composed of a constituting unit derived from a hydrophilic monomer selected from the group consisting of acrylamide and an acrylamide derivative,
   the block copolymer (A) is contained in a proportion of 20 to 80% by weight relative to the total weight of the block copolymer (A) and the homopolymer (B) such that the lubrication layer is configured to provide surface lubricity and swellability, and
   the block copolymer (A) is crosslinked or polymerized such that the block copolymer (A) forms a mesh structure.

18. The laminate structure according to claim 17, wherein the reactive monomer is at least one selected from the group consisting of glycidyl acrylate, glycidyl methacrylate (GMA), 3,4-epoxycyclohexylmethyl acrylate, 3,4-epoxycyclohexylmethyl methacrylate, β-methylglycidyl methacrylate, and allyl glycidyl ether.

19. The laminate structure according to claim 17, wherein the hydrophilic monomer composing the block copolymer (A) is at least one selected from the group consisting of N-methylacrylamide, N,N-dimethylacrylamide, and acrylamide.

20. The laminate structure according to claim 17, wherein the base layer comprises a multilayer structure including a core portion and at least one surface layer.

\* \* \* \* \*